United States Patent [19]

Shen

[11] Patent Number: 5,749,854
[45] Date of Patent: May 12, 1998

[54] PNEUMATIC CONTROLLED INFUSION DEVICE

[76] Inventor: Chung-Shan Shen, Suite 2, 7F, No. 95-8 Chang Ping Road, Sec. 1, Taichung, Taiwan

[21] Appl. No.: 661,468

[22] Filed: Jun. 11, 1996

[51] Int. Cl.[6] ................................................ A61M 37/00
[52] U.S. Cl. .................... 604/131; 604/118; 604/140; 604/141; 604/247
[58] Field of Search ........................... 604/9, 118, 121, 604/131, 132, 133, 140, 141, 142, 143, 146, 147, 247

[56] References Cited

U.S. PATENT DOCUMENTS

| | | | |
|---|---|---|---|
| 4,657,160 | 4/1987 | Woods et al. | 604/141 X |
| 4,673,392 | 6/1987 | Keime | 604/141 |
| 4,781,674 | 11/1988 | Redmond et al. | 604/247 X |
| 4,861,340 | 8/1989 | Smith et al. | 604/141 |
| 4,904,236 | 2/1990 | Redmond et al. | 604/247 X |
| 5,013,303 | 5/1991 | Tamari et al. | 604/140 |
| 5,137,522 | 8/1992 | Bron | 604/247 |
| 5,147,310 | 9/1992 | Giannini et al. | 604/141 |
| 5,240,035 | 8/1993 | Aslanian et al. | 604/247 X |
| 5,279,568 | 1/1994 | Cater | 604/131 X |
| 5,346,477 | 9/1994 | Edwards et al. | 604/141 |

*Primary Examiner*—Sam Rimell
*Assistant Examiner*—Robert V. Racunas

[57] ABSTRACT

A pneumatic controlled infusion bag comprises a double-layer infusion bag, a space defined between the layers for receiving pneumatic pressure therein to gradually squeeze the medicament inside the bag delivering into the vessel of a patient. A pneumatic fluid control assembly controllably supplies the pneumatic pressure into the infusion bag. The assembly comprises an air inlet connected to a pneumatic source, an outlet connected to the bag via a hose, a first and a second piston disposed inside the assembly for respectively controlling the open/close and the proper amount of the pneumatic pressure. A pressure release valve inside the infusion bag can automatically release the excessive pneumatic pressure out of the bag. This disclosure overcomes the resistance of the blood pressure and needs no longer to form a potential difference between the infusion bag and the human body.

7 Claims, 4 Drawing Sheets

PNEUMATIC CONTROLLED INFUSION DEVICE

BACKGROUND OF THE INVENTION

The present invention relates to infusion device for injecting medicaments and more particularly to a pneumatic controlled infusion device which is portable and can be applied at any position lower than the elevation of the needle cannula.

Blood in human body is pumped by heart beat and circulates everywhere within the body via the blood vessels, therefore, blood pressure occurs in the vessels. This causes problem of that the blood pressure resists the injection of the medicament into human body. If the infusion bottle or bag is positioned lower than the needle cannula, the medicament will not be entered into the vessel. Thus, the medical man suspends the infusion bottle from a stand to obtain potantial difference to overcome the resistance of the blood pressure so as to accomplish an intravenous injection. However, this manner of infusion causes a lot of inconviences such as that a patient under infusion of medicament must lie down there motionless for hours. If the patient has to move for further examination or to go to the lavatory, he must elevate the infusion bottle over head to maintain the potential different, unless, the infusion will be interrupted or causing a blood retraction with medicament into the needle cannula.

SUMMARY OF THE PRESENT INVENTION

The present invention has a main object to provide a pneumatic controlled infusion device which is portable and can be applied at any position lower than the elevation of the needle cannula.

Another object of the present invention is to provide a pneumatic controlled infusion device which facilitates the movement of the patient that the patient is no longer required to lie down there motionless for hours during medicament infusion.

Accordingly, the pneumatic controlled infusion device of the present invention comprises generally an infusion bag and a pneumatic fluid control assembly. The bag is composed of an external wall which is made of tensile material, an internal wall which is made of flexible material and contains the medicament therein, a space defined between the two walls and communicating to an air inlet at the bottom of the bag, a pressure release valve adjacent the air inlet and a closed medicament outlet adjacent the pressure release valve. The medicament outlet is pierceable by a needle cannula at infusion.

The pneumatic control assembly comprises a spherical body, a transverse circular hole through the body and separated by a vertical partition at the middle of the hole to define a pair of first and second cylindrical chambers which are communicated by a aperture at the center of the partition, an air inlet at the top and an air outlet at the bottom thereof communicated with and perpendicular to the chambers, a pair of first and second piston members respectively inserted into the chambers and biased respectively by a pair of spring means and a pneumatic source connects to the air inlet. The first piston inserts into the first chamber for controlling the pneumatic fluid entered into the first chamber and the second piston inserts into the second chamber for controlling the amount of the pneumatic fluid supplied into the infusion bag via a hose. When the syringe cannula from the bag pierced into the vessel of a patient, the internal wall of the bag will be squeezed contripetally under appropriate pneumatic pressure and delivers proper amount of the medicament into the patient body.

The present invention will become more fully understood by reference to the following detailed description thereof when read in conjunction with the attached drawings.

DETAILED DESCRIPTION OF THE PREFERRED EMBODIMENT

Figure 1:
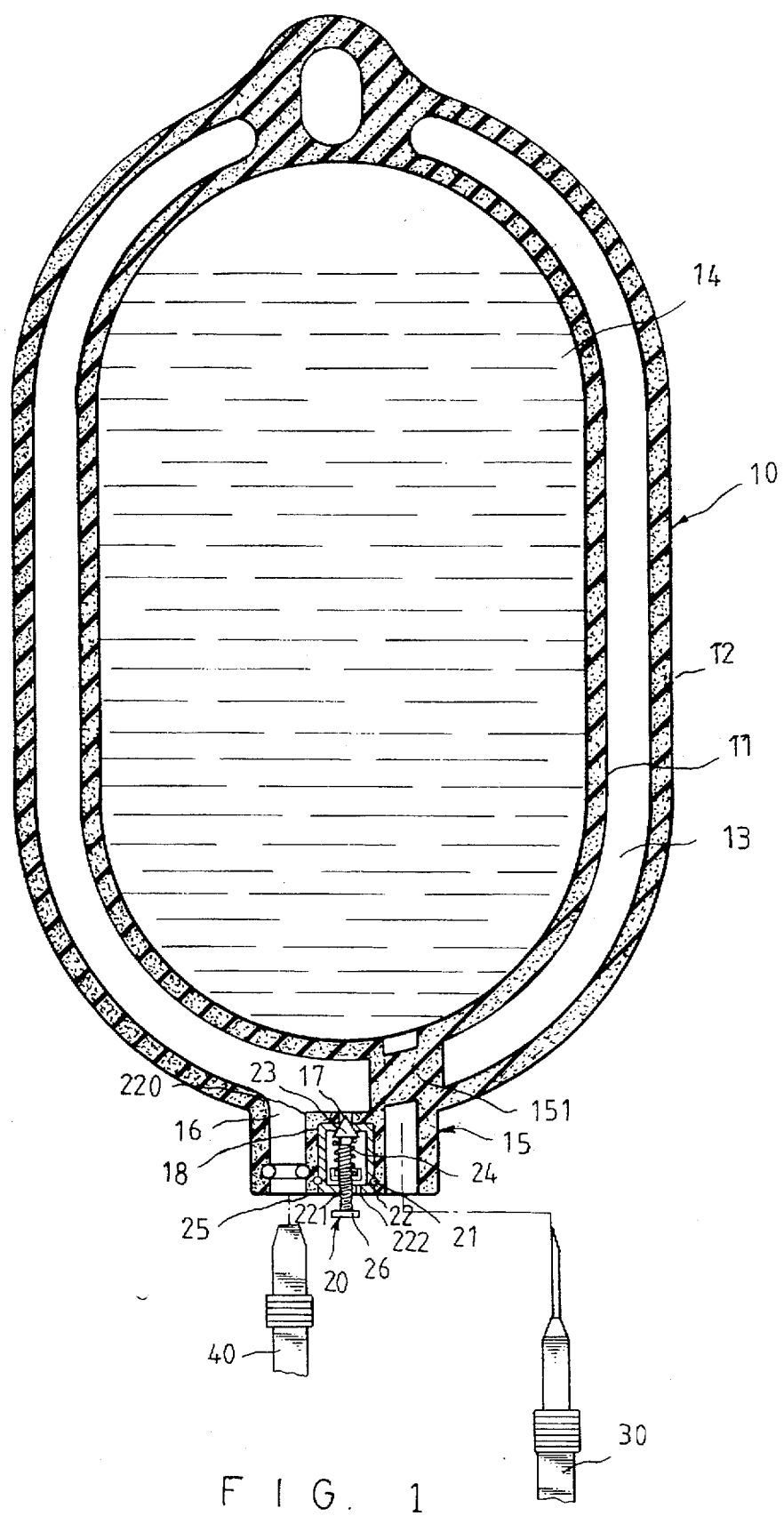
FIG. 1 is a sectional view to show an infusion bag of the preferred embodiment according to the present invention.
Figure 2:
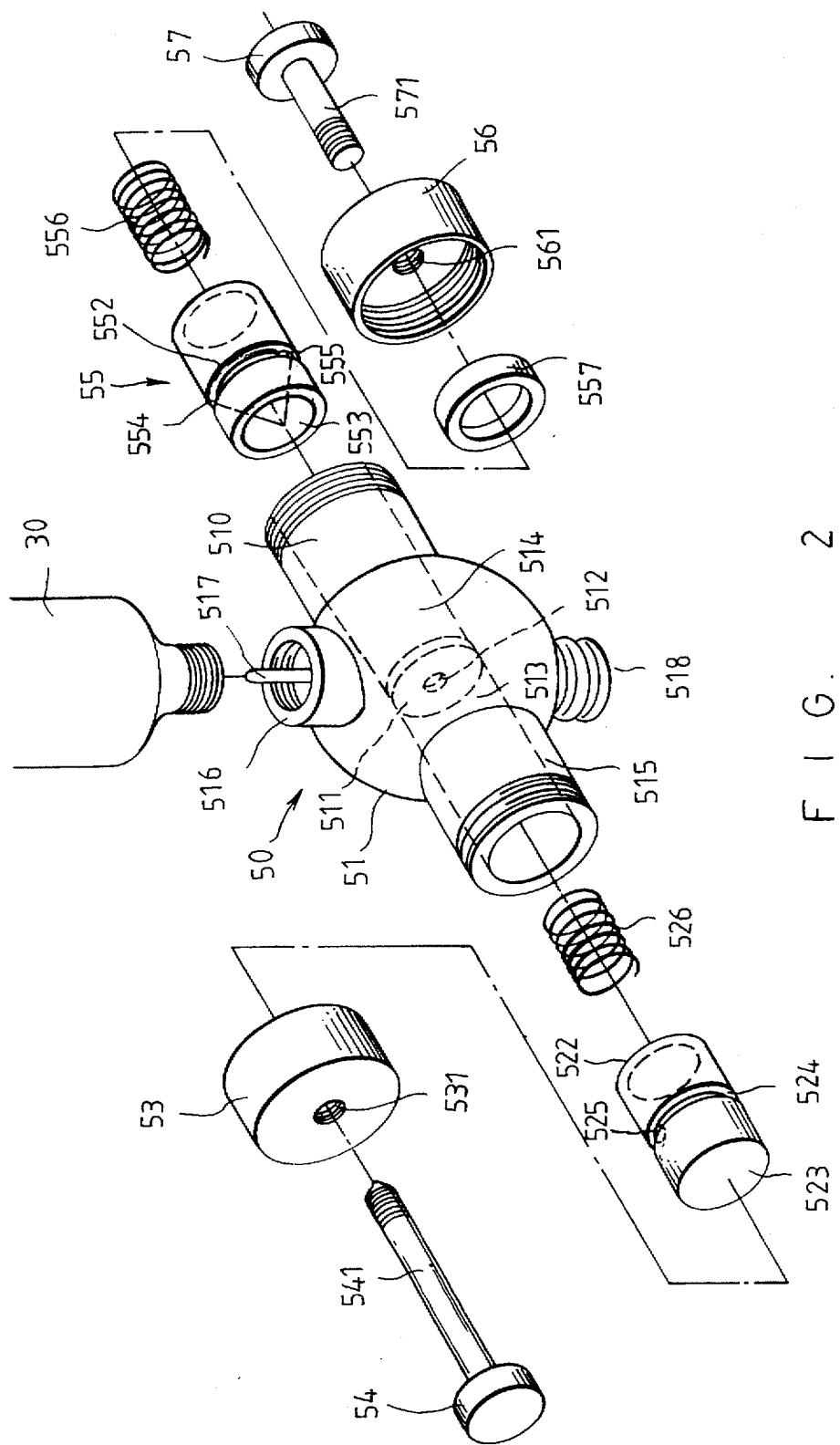
FIG. 2 is an exploded perspective view to show a spherical body of the pneumatic fluid control assembly of the preferred embodiment according to the present invention.

With reference to FIGS. 1 and 2 of the drawings, the pneumatic controlled infusion device of the present invention comprises generally an infusion bag 10 and a pneumatic fluid control assembly 50.

The infusion bag 10 comprises an internal wall 11 which is made of flexible material and contains proper amount of the medicament 14 therein, an external wall 12 which is made of tensile material and connects with the internal wall 11 at their corresponding top and bottoms, a space 13 defined between the two walls for receiving pneumatic pressure therein, a tubular outlet 15 at a bottom communicated with the medicament including a blockage 151 which is pierceable by a syringe needle 30, a tubular air inlet 16 at a bottom symmetrical to the outlet 15 and communicated with the space 13 which is insertable by a hose 40 and an air outlet 17 abutting a cylinder chamber 18 formed at the bottom between the outlet 15 and the inlet 16. A pressure release valve 20 secured into the cylinder chamber 18 and sealed by a sealing ring 21. The valve 20 has a cylinder housing 22, an air inlet 220 at the top of the housing 22 made in registry with the outlet 17, a threaded hole 221 at the center of the bottom thereof abutting a pair of recesses 222, a taper headed plunger 23 axially inserted into the air inlet 220 and biased by a spring 24 and stopped against a cap 25 which is held by an adjustable threaded pin 26 screwed into the housing 22 via the threaded hole 221. The arrangement of the pressure release valve 20 in the infusion bag 10 tends to maintain the pneumatic pressure in the space 13 at a appropriate level. If the pneumatic pressure exceeds a predetermined limit, it will press the plunger 23 moving backwards to release the excessive pressure out of the valve 20, thus, providing further protection against an out controlled medicament injection.

Figure 3:
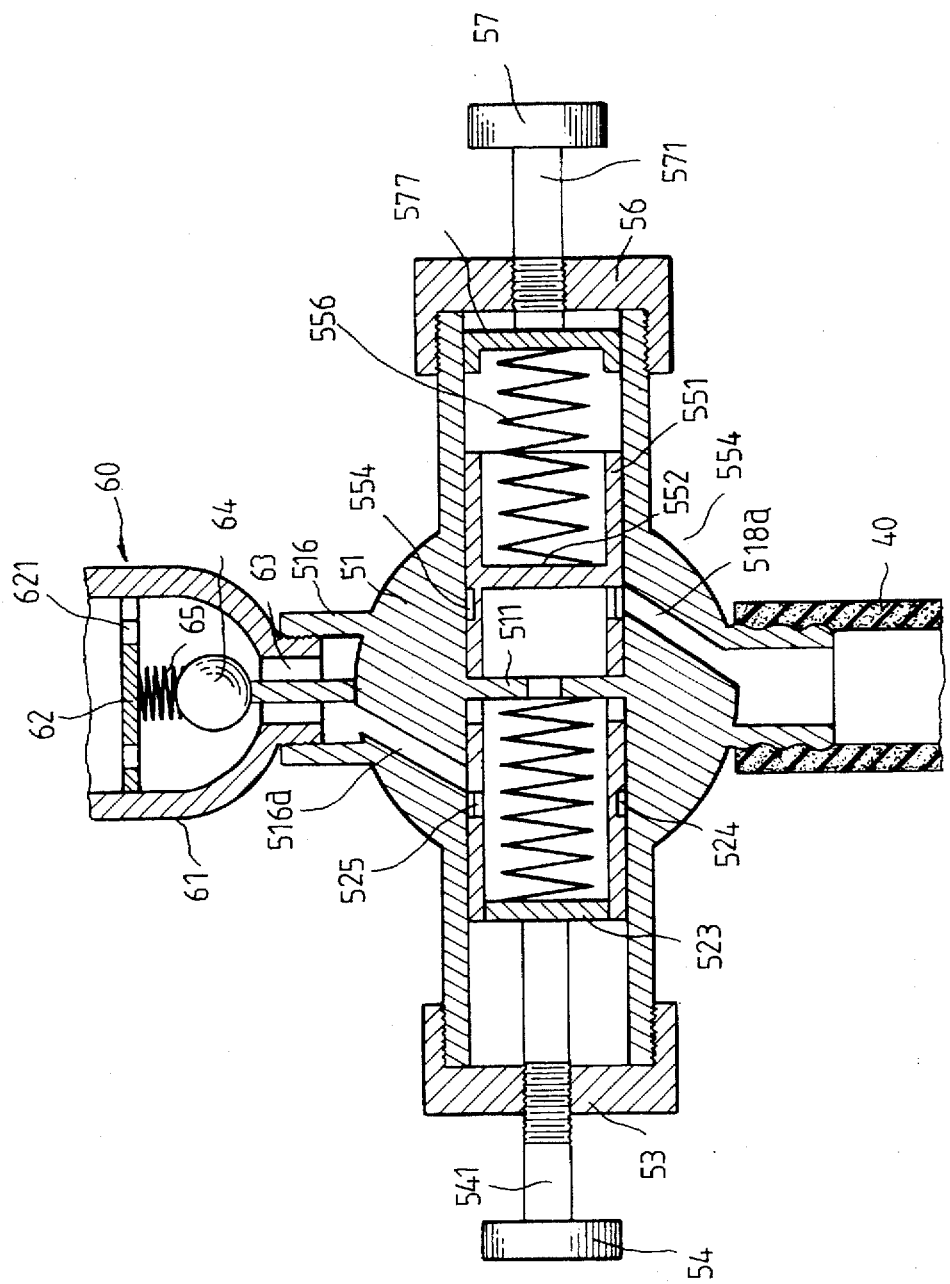
FIG. 3 is a sectional view to show a pneumatic fluid control assembly of the present invention.

The pneumatic fluid control assembly 50 comprises a spherical body 51, a transverse circular hole 510 radially extended through the body 51 and separated by a vertical partition 511 at the middle of the hole 510 thus defining a first and a second chamber 513 and 514 therebetween and communicated by an aperture 512 at the center of the partition 511, each of the chambers 513 and 514 has a tubular extension 515 projected outward from body 51 each having outer thread at free end thereof, a tubular air inlet 516 projected upward from the top of the body 51 which has a threaded inner periphery, a stem 517 projected upward from the center thereof and a first air passage 516a extended between the air inlet 516 and the first chamber 513 therethrough and a tubular air outlet 518 on the bottom of the body 51 which has a corrugated outer periphery for engaging the other end of the hose 40 thereon and a second air passage 518a extended between the air outlet 518 and second chamber 514 therethrough (as shown in FIG. 3). A first piston 52 has a hollow cylinder member 521 including an opened end 522 towards the partition 511, a closed end 523 towards outward, an annular groove 524 around an outer periphery and an air inlet 525 inside the groove 524 through the body 51 thereof, a first coil spring 526 axially inserted into the cylinder member 521 and biased between the partition 511 and the cylinder member 521 which the cylinder member 521 is slidingly inserted into the first chamber 513. A first cap 53 has a threaded inner periphery for fastening the cap 53 onto the free end of the extension 515 of the first chamber 513 and threaded central bore 531 for permitting a first adjustable bolt 54 screwed into the chamber 513. The bolt 54 has an elongated shank 541 stopped against the closed end of the cylinder member 521. A second piston 55 comprises a hollow cylinder member 551 which has two ends opened, a second vertical partition 552 at the middle of the cylinder member 551, a cone 553 projected inwards from the inner side of the partition 552 with the conical point towards the aperture 512 of the partition 511 and slightly exceeding the inward end of the cylinder member 551, an annular groove 554 around an outer periphery thereof abutting the foot of the cone 553 and an air outlet 555 inside the groove 554 through the body thereof. The cylinder member 551 is inserted into the second chamber 514 with the conical point thereof stopped against the aperture 512 of the partition 511 therein. A second coil spring 556 inserts into the outward end of the cylinder member 551 and is held by a sleeve 557. A second cap 56 has threaded inner periphery for fastening onto the free end the extension 515 of the second chamber 514 and a threaded central bore 561 on the bottom thereof for permitting a second adjustable bolt 57 screwed into the chamber 514. The bolt 57 has a shorter threaded shank 571 stopped against the outward surface of the sleeve 557.

Referring to FIG. 3 which is a sectional view to show an assembled pneumatic fluid control assembly 50 as described in the above instance. A pneumatic source 60 now is fastened into the air inlet 516 of the spherical body 51, the pneumatic source 60 is a small bottle having reinforced housing 61 a third partition 62 including a plurality of recesses 621 therein positioned perpendicular to the axis and in the proximity of an opening 63 and a ball stopper 64 biased by a coil spring 65 blocking the opening 63 to prevent the pneumatic pressure from leak out. The bottle 60 contains the pneumatic source equal to several times of the volume of the infusion bag 10. When it is fastened into the inlet 516, the ball stopper 64 will be pushed by the stem 517 and moves inward permitting the pneumatic pressure to flow into the first air passage 516a. The pneumatic pressure is normally prevented by the cylinder member 521 of the first piston 52 from entering into the first chamber 513 because the cylinder member 521 is urged by the first spring 526 and stopped at an outward position where the inlet 525 disagrees with the first air passage 516a. The cylinder member 551 of the second piston 55 is biased by second spring 556 under appropriate tension force so as to force the conical point of the cone 553 stopped against the aperture 512 of the partition 511.

Figure 4:
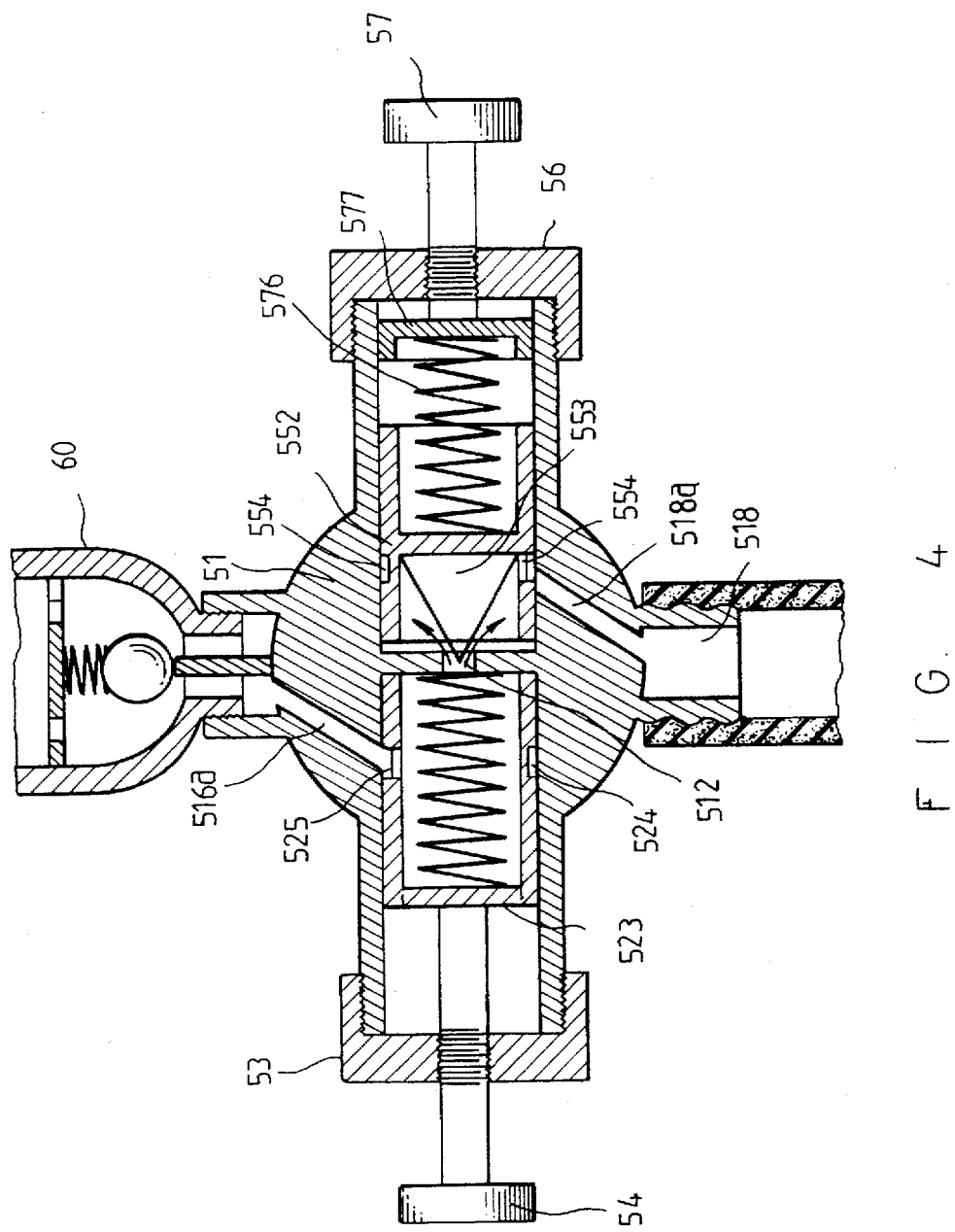
FIG. 4 is a sectional view of FIG. 3 under operation.

Referring to FIG. 4, at infusion, first connect the hose 40 between the infusion bag 10 and the pneumatic fluid control assembly 50 and pierce the syringe cannula 30 into the medicament 14 of the bag 10 to lead the medicament 14 flowing into the tube and pierce a second syringe cannula at the other end of the tube into a vessel of a patient, then, fasten the first adjustable bolt 54 to displace the cylinder member 521 inward as to stop the lateral surface of the partition 511 so that the air inlet 525 therein can agree with the first air passage 516a and permit the pneumatic fluid flowing into the first chamber 513. When the pressure of the pneumatic fluid becomes higher than the tension force of the second coil spring 556, the conical point of the cone 553 will be pushed backward to leave an appropriate clearance allowing the pneumatic fluid in proper pressure passing through the aperture 512 and entered into the space 13 of the bag 10 via the second air passage 518a, the hose 40 and the inlet 16, in order to press the internal wall 11 of the bag 10 delivering proper amount of the medicament 14 into the vessel of the patient for a proper intravenous injection. If the pneumatic pressure in the first chamber 513 becomes too high or too low, operate the second adjustable bolt 57 to adjust the tension force of the second coil spring to obtain a pressure balancement therebetween. Further, if the pneumatic pressure becomes too high in the space 13 of the bag 10, the pressure release valve 20 at the bag 10 will automatically release the excessive pressure and insures the delivery of the medicament always in proper manner. When the medicament 14 in the bag 10 is finished, unfasten the first adjustable bolt 54 so that cylinder member 521 is urged by the first coil spring to displace outward to a normal position to stop further supplying of the pneumatic fluid via the first air passage 516a. When the pneumatic source is removed from the inlet 516, the opening 63 is blocked by the ball stopper 64 again and the remainder can be useful to apply next infusion bag 10.

Based on the aforediscussed instances, the pneumatic controlled infusion device of the present invention provides a great convenience to the user that the medic has no longer to suspend the infusion bag from a stand to obtain a potential different and the patient can carry the infusion device in his pocket in whatever gesture and moves everywhere as he wishes.

Note that the specification relating to the above embodiment should be construed as examplary rather than as limitative of the present invention, with many variations and modifications being readily attainable by a person of average skill in the art without departing from the spirit or scope thereof as defined by the appended claims and their legal equivalents.

I claim:

1. A pneumatic controlled infusion device comprising:
    an infusion bag, said bag having an internal wall for containing a predetermined amount of medicament therein and an external wall connected together with the internal wall at their corresponding upper and lower portions, a receiving space being defined between said internal and external walls for receiving pneumatic pressure therein, a tubular air outlet at a bottom communicating with the medicament including a pierceable blockage therein, a tubular air inlet at a bottom symmetrical to said outlet and communicating to said receiving space and insertable by an external hose therein and a hollow cylinder chamber having a central recess communicating with said receiving space and an outward opening formed at a bottom between said air inlet and outlet, said cylinder chamber being provided to secure a pressure release valve therein which is sealed by a sealing ring;
    a pneumatic fluid control assembly connected with said infusion bag via said tubular air inlet by a hose, said control assembly comprising a spherical body, a transverse circular hole radially extended through the body thereof and separated by a first vertical partition at a middle of said hole which defines a first and a second chamber by said partition, an aperture formed at a center of said partition for communicating said chambers, each of said chambers having a tubular extension projected outward from said body and each of said extensions having a threaded outer periphery at a free end thereof, a tubular air inlet projected upward from said body, said air inlet having a threaded inner periphery, a stem projected upward from a center therein and communicated to said first chamber via a first air passage, a tubular outlet projected downward from a bottom of said body and communicated to said second chamber via a second air passage therebetween, said tubular outlet having a corrugated outer periphery engageable with an other end of said hose, a first piston slidingly disposed into said first chamber and secured by a first cap onto the free end of said extension for operating said pneumatic fluid control assembly, a second piston slidingly disposed into said second chamber and secured by a second cap onto the free end of said second extension for adjusting the amount of pneumatic fluid passing through the aperture of said partition, said first and second caps each having a threaded inner periphery and a threaded central bore at a bottom thereof, and a pneumatic source engaged into said tubular inlet of said body and opened by said stem for supplying pneumatic fluid into said body.

2. A device as recited in claim 1 wherein said internal wall of said infusion bag is made from flexible material.

3. A device as recited in claim 1 wherein said external wall of said infusion bag is made from tensile material.

4. A device as recited in claim 1 wherein said pressure releasing valve comprises a cylinder housing having an air inlet at a center of an inward wall thereof which is made in registry with the air outlet of said hollow cylinder chamber and a threaded hole at a center of an outward wall adjacent a pair of recesses thereabout, a taper headed plunger axially engaged into said air inlet and biased by a coil spring and a cap means and a threaded pin screwed into said housing via said threaded hole and adjustably stopped against said cap means.

5. A device as recited in claim 1 wherein said first piston comprises a hollow cylinder member having an opened end toward said partition of said spherical body, an annular groove around an outer periphery and an air inlet formed inside said groove engageable with said first air passage, a first coil spring axially inserted into said opened end and biased between said first hollow cylinder member and said partition and a first adjustable bolt screwed into said first chamber via the threaded hole of said first cap and adjustably stopped against an outward end of said first hollow cylinder member thereon.

6. A device as recited in claim 1 wherein said second piston comprises a hollow cylinder member having two opened ends, a second vertical partition formed inside said cylinder member at a middle portion thereof, a cone projected inward from an inward surface of said partition with a conical point thereof exceeded an inward end of said cylinder member and stopped into the aperture of said first vertical partition and an annular groove including an air outlet therein formed around an outer periphery abutting a foot of said cone, a second coil spring inserted into an outward end of said cylinder member and biased between said cylinder member and a sleeve and secured by a second cap at a free end of the extension of said second chamber, which has a threaded inner periphery and a threaded central hole and a second adjustable bolt axially screwed into said second chamber via said threaded central hole and adjustably stopped against an outward surface of said sleeve.

7. A device as recited in claim 1 wherein said pneumatic source comprises a reinforced housing, a third partition formed perpendicular to the axis and in the proximity of an opening thereof, a plurality of recesses in said partition, a ball stopper stopped the opening and biased by a coil spring between said stopper and said partition.

* * * * *